(12) United States Patent
Gouda et al.

(10) Patent No.: US 10,509,039 B2
(45) Date of Patent: Dec. 17, 2019

(54) INTEGRATED PHOSPHOR NANOPARTICLE MARKING AGENT, AND FLUORESCENT IMMUNOSTAINING EMPLOYING SAME

(71) Applicant: Konica Minolta, Inc., Tokyo (JP)

(72) Inventors: Hideki Gouda, Tokyo (JP); Masaru Takahashi, Musashino (JP)

(73) Assignee: KONICA MINOLTA, INC., Tokyo (JP)

( * ) Notice: Subject to any disclaimer, the term of this patent is extended or adjusted under 35 U.S.C. 154(b) by 89 days.

(21) Appl. No.: 15/123,578

(22) PCT Filed: Mar. 4, 2015

(86) PCT No.: PCT/JP2015/056357
§ 371 (c)(1),
(2) Date: Sep. 2, 2016

(87) PCT Pub. No.: WO2015/133523
PCT Pub. Date: Sep. 11, 2015

(65) Prior Publication Data
US 2017/0074886 A1   Mar. 16, 2017

(30) Foreign Application Priority Data

Mar. 6, 2014 (JP) ................................ 2014-043847

(51) Int. Cl.
*G01N 33/58* (2006.01)
(52) U.S. Cl.
CPC ................... *G01N 33/587* (2013.01)
(58) Field of Classification Search
CPC .. G01N 33/54346; G01N 33/587; B82Y 5/00; B82Y 15/00
See application file for complete search history.

(56) References Cited

U.S. PATENT DOCUMENTS

2012/0183980 A1   7/2012   Kim

FOREIGN PATENT DOCUMENTS

EP       1790706 A1   5/2007
JP    2008175750 A    7/2008
(Continued)

OTHER PUBLICATIONS

Pierce Catalog. Avidin-biotin Products. Pierce Biotechnology 2005, USA. (Year: 2005).*

(Continued)

*Primary Examiner* — Shafiqul Haq
(74) *Attorney, Agent, or Firm* — Lucas & Mercanti, LLP (57) ABSTRACT

Provided are: a phosphor-integrated nanoparticle labeling agent which is capable of yielding a sufficient signal intensity even when its final concentration in an immunofluorescent staining reaction system is low (e.g., 0.02 nM) and enables to obtain an immunofluorescently stained image with reduced noise by inhibiting non-specific adsorption of a probe biological substance and a label to substances other than a detection subject; and an immunostaining method using the same. The phosphor-integrated nanoparticle labeling agent is a set which includes: a probe biological substance 3, which is linked to a first binding group substance A via a first hydrophilic polymer-derived spacer 1 having a length of 30 Å to 1,000 Å and specifically binds to a biomolecule 2; and a phosphor-integrated nanoparticle 5, which has a second binding group substance B capable of specifically binding to the first binding group substance A.

7 Claims, 2 Drawing Sheets

(56) References Cited

FOREIGN PATENT DOCUMENTS

| WO | 20120029342 A1 | 3/2012 |
| WO | 2012133047 A1 | 10/2012 |
| WO | 2013035688 A1 | 3/2013 |
| WO | 20130035703 A1 | 3/2013 |

OTHER PUBLICATIONS

Extended European Search Report dated Sep. 11, 2017 from European Application No. 15758624.9-1405 / 3115783 PCT/JP2015056357.
Notification of Reasons for Refusal dated Dec. 1, 2015 from corresponding Japanese Patent Application No. JP 2015-540775 and English translation.
Decision of Refusal dated Apr. 5, 2016 from corresponding Japanese Application No. JP 2015-540775 and English translation.
Thermo Scientific Avidin-Biotin Technical Handbook; 2009; p. 8 and p. 12.
User Guide: EZ-Link NHS-PEG12-Biotin, 2011.
International Search Report dated May 26, 2015 for PCT/JP2015/056357 and English translation.
Written Opinion dated May 26, 2015 for PCT/JP2015/056357 and English translation.
Office Action dated Apr. 5, 2016 for corresponding Japanese Patent Application No. 2015-540775.
Appeal Board's Decision to Grant a Patent mailed on Apr. 4, 2017 from corresponding Japanese Patent Application No. JP 2015-540775 and English translation.

* cited by examiner

N-C: 5   (0.71+0.75)X5=7.3
C-C: 15  (0.75+0.75)X15=22.5
C-O: 22  (0.75+0.63)X22=30.36
        Total length: 60.16 A

INTEGRATED PHOSPHOR NANOPARTICLE MARKING AGENT, AND FLUORESCENT IMMUNOSTAINING EMPLOYING SAME

CROSS REFERENCE TO RELATED APPLICATION

This Application is a 371 of PCT/JP2015/056357 filed on Mar. 4, 2015 which, in turn, claimed the priority of Japanese Patent Application No. JP 2014-043847 filed on Mar. 6, 2014, both applications are incorporated herein by reference.

TECHNICAL FIELD

The present invention relates to a phosphor-integrated nanoparticle labeling agent and an immunofluorescent staining method using the phosphor-integrated nanoparticle labeling agent.

BACKGROUND ART

Conventionally, phosphor-integrated nanoparticle labeling agents are known (for example, Patent Document 1). These phosphor-integrated nanoparticle labeling agents comprise: a probe biological substance capable of binding to a biomolecule to be detected; and a phosphor-integrated nanoparticle.

In Patent Document 1, it is disclosed that, when a first binding group (for example, biotin in Examples (the same applies hereinafter)) is linked to the probe biological substance (primary antibody=anti-HER2 antibody) capable of binding to the biomolecule to be detected (HER2) and a second binding group (streptavidin) capable of binding to the first binding group is linked to the phosphor-integrated nanoparticle, a spacer having an appropriate chain length may be allowed to exist between the first binding group and the probe biological substance as well as between the second binding group and the phosphor-integrated nanoparticle. As a specific example of a linker used for the preparation of the spacer that links the second binding group with the phosphor-integrated nanoparticle, $SM(PEG)_{12}$ is used in Examples of Patent Document 1. Further, in Patent Document 1, it is also disclosed that, not only an embodiment in which the primary antibody is bound to the phosphor-integrated nanoparticle via a biotin-streptavidin bond as shown in Examples, but also an embodiment in which a secondary antibody is bound to the primary antibody and then the phosphor-integrated nanoparticle is allowed to bind to the secondary antibody via a biotin-streptavidin bond can be adopted.

PRIOR ART REFERENCE

Patent Document

[Patent Document 1] WO 2013/035688

SUMMARY OF THE INVENTION

Problems to be Solved by the Invention

In immunofluorescent staining using such a conventional phosphor-integrated nanoparticle labeling agent as described in Patent Document 1, the intensity of a fluorescence signal, that is, the certainty that the presence of a substance to be detected is indicated by bright spots can be improved to a certain extent by increasing the concentration of the probe biological substance and/or phosphor-integrated nanoparticle; however, at the same time, since this makes non-specific adsorption of the probe biological substance and phosphor-integrated nanoparticle to a substance other than the substance to be detected more likely to occur, there is a problem that bright spots also appear at those spots where the substance to be detected is absent, which means an increased noise.

The present invention was made with a focus on this problem, and objects of the present invention are: to provide a phosphor-integrated nanoparticle labeling agent which is capable of yielding a sufficient signal intensity even when the final concentration of its phosphor-integrated nanoparticle is low (e.g., 0.02 nM) and enables to obtain an immunofluorescently stained image with reduced noise by inhibiting non-specific adsorption of a probe biological substance and a label to substances other than a detection subject; and to provide an immunostaining method using the same.

Technical Solution

By the present invention, the below-described phosphor-integrated nanoparticle labeling agent and an immunofluorescent staining method using the same are provided.

In order to realize at least one of the above-described objects, the image-forming apparatus that reflects one aspect of the present invention comprises a set composed of: a probe biological substance which is linked to a first binding group substance via a polymer-derived spacer having a length of 30 Å to 1,000 Å and specifically binds to a biomolecule; and a phosphor-integrated nanoparticle which comprises a second binding group substance capable of specifically binding to the first binding group substance.

In order to realize at least one of the above-described objects, the immunofluorescent staining method that reflects one aspect of the present invention is characterized in that it is performed using the above-described phosphor-integrated nanoparticle labeling agent.

Advantageous Effects of Invention

According to the present invention, a sufficient signal intensity can be obtained even when the final concentration of the phosphor-integrated nanoparticle is low (e.g., 0.02 nM) and an immunofluorescently stained image with reduced noise can be obtained by inhibition of non-specific adsorption of a probe biological substance and a label to substances other than a detection subject.

MODE FOR CARRYING OUT THE INVENTION

Figure 1:
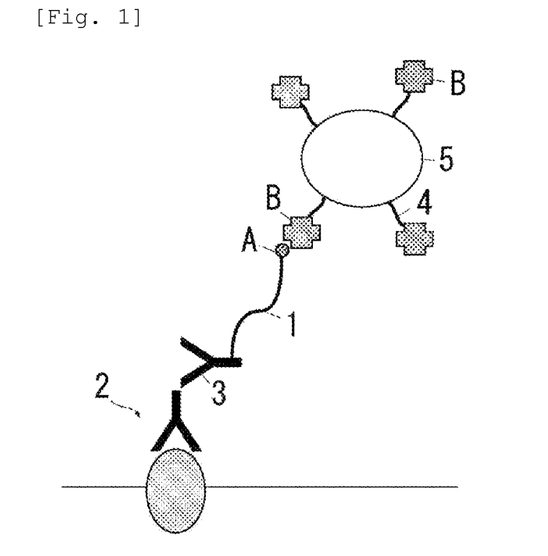
FIG. 1 is a drawing that illustrates a state of immunofluorescent staining performed using the phosphor-integrated nanoparticle labeling agent of the present invention.

As shown in FIG. 1, the phosphor-integrated nanoparticle labeling agent of the present invention is characterized by comprising a set composed of: a probe biological substance 3, which is linked to a first binding group substance A via a polymer-derived spacer 1 and specifically binds to a biomolecule 2; and a phosphor-integrated nanoparticle 5, to which a second binding group substance B capable of specifically binding to the first binding group substance A is bound.

<<Biomolecule>>

In the present invention, the "biomolecule" is not particularly restricted and may be, for example, an antigen or a primary to n-order antibody (reagent I) specifically bound to the antigen. In the present invention, the term "antibody" is used with a meaning that includes arbitrary antibody fragments and derivatives, encompassing a variety of antibodies such as Fabs, Fab'2s, CDRs, humanized antibodies, multifunctional antibodies and single-chain antibodies (ScFv).

(Antigen)

Examples of the "antigen" include proteins (e.g., polypeptides and oligopeptides) and amino acids (including modified amino acids) as well as complexes formed by a protein or amino acid with a saccharide (e.g., oligosaccharide, polysaccharide or sugar chain), lipid or modified molecule thereof. Specifically, the "antigen" may be, for example, but not particularly restricted to, a tumor marker, a signal transducer or a hormone.

Examples of the "antigen" also include cancer-associated antigens, such as cancer growth regulators, metastasis regulators, growth regulator receptors and metastasis regulator receptors; inflammatory cytokines, such as TNF-α (Tumor Necrosis Factor α) and IL-6 (Interleukin-6) receptors; and virus-associated molecules such as RSV F protein.

In an immunofluorescent staining method, when the probe biological substance is not directly bound to an antigen but is fixed on the antigen via a primary to n-order antibody, the "biomolecule" to which the probe biological substance specifically binds is the primary to n-order antibody (reagent I) specifically bound to the antigen and the probe biological substance is thus a secondary to (n+1)-order antibody.

As the above-described antibody, for example, an antibody drug that is generally used for the treatment of autoimmune diseases such as rheumatoid arthritis, malignant tumors such as cancer, viral infection and the like can be used.

Table 1 below shows representative antibody drugs that are clinically used. It is noted here that, in Table 1, antibody drugs used for the treatment of an autoimmune disease or infectious disease are also shown for reference.

<<Probe Biological Substance>>

The probe biological substance is a molecule that specifically binds to the "biomolecule" and, as described above, when the "biomolecule" is an antigen or a primary to n-order antibody (reagent I), a primary antibody or a secondary to (n+1)-order antibody corresponds to the "probe biological substance".

In the case shown in FIG. 1, the probe biological substance 3 is chemically bound to one end of the polymer-derived spacer 1.

The chemical bond between the spacer 1 and the probe biological substance 3 is a bond formed by an appropriate bonding mode such as covalent bonding, ionic bonding, hydrogen bonding, coordinate bonding, physical adsorption or chemical adsorption and, from the standpoint of the bonding strength, it is preferably a covalent bond such as an amide bond, an ester bond, an imide bond or a bond utilizing addition of thiol to a maleimide group.

Specific examples of a method of chemically bonding the probe biological substance 3 to one end of a polymer include a thiol group-maleimide group coupling reaction method; a cross-linking reaction method using a cross-linking agent (e.g., 1-ethyl-3-(3-dimethylaminopropyl)carbodiimide (EDC)); and an ionic bonding method.

<<Polymer>>

As a polymer used for the formation of the spacer 1, a hydrophobic polymer or hydrophilic polymer that has a prescribed length or a combination thereof is suitably used.

Examples of the hydrophobic polymer include polyamides, saturated hydrocarbons, cyclic hydrocarbons, hydrophobic polyamino acids, polystyrenes and polymethacrylates, which have a prescribed length as described below.

The hydrophilic polymer is not particularly restricted and, for example, one or more hydrophilic polymers selected from the group consisting of polyethylene glycols, polypropylene glycols, ficoll, polyvinyl alcohols, styrene-maleic anhydride alternating copolymers, divinyl ether-maleic anhydride alternating copolymers, polyvinylpyrrolidones, polyvinylmethyl ethers, polyvinylmethyloxazolines, polyethyloxazolines, polyhydroxypropyloxazolines, polyhydroxypropyl methacrylamides, polymethacrylamides, polydimethyl acrylamides, polyhydroxypropyl methacrylates, polyhydroxyethyl acrylates, hydroxymethyl cellulose, hydroxyethyl cellulose, polyaspartoamides, synthetic polyamino acids and equivalents thereof can be used. Among the above-exemplified hydrophilic polymers, a poly-

TABLE 1

Representative Antibody Drugs

| Target disease | Common name | Trade name | Target molecule |
| --- | --- | --- | --- |
| Cancer and related disease | Rituximab | Rituxian (registered trademark) | CD20 |
| | Gemutuzumab | Mylotarg (registered trademark) | CD33 |
| | Alemtuzumab | Campath (registered trademark) | CD52 |
| | Ibritumomab | Zevalin (registered trademark) | CD20 |
| | Tositumomab | Bexxar (registered trademark) | CD20 |
| | Trastuzumab | Herceptin (registered trademark) | HER2 |
| | Bevacizumab | Avastin (registered trademark) | VEGF |
| | Cetuximab | Erbitux (registered trademark) | EGF receptor |
| | Panitumumab | Vectibix (registered trademark) | EGF receptor |
| Autoimmune disease | Infliximab | Remicade (registered trademark) | TNF-α |
| Infectious disease | Palivizumab | Synagis (registered trademark) | RSV F protein | ethylene glycol (PEG) is preferred because the chain length thereof can be easily set based on the number of oxyethylene units.

It is preferred that the above-described polymer be obtained as a polymer that is maleimidated, aminated, biotinylated, thiolated or the like by the below-described reaction and subsequently bound as a linker reagent to the probe biological substance 3 and the first binding group substance A.

The above-described polymer can be obtained in the form of a linker by, for example, a method of synthesizing a polymer having an amino group at both ends through an amidation reaction from an alkanedicarboxylic acid and an diamino alkane, a method of allowing an amino group-containing polymer to react with biotin-4-nitrophenyl ester and thereby biotinylating the amino group, or a method of allowing an amino group-containing polymer to react with N-succinimidyl-3-maleimidopropionate and thereby maleimidating the amino group.

In this case, it is preferred to select the alkanedicarboxylic acid and diaminoalkane used for the synthesis such that the main chain of the resulting polymer (which may contain a heteroatom(s) in addition to carbon atoms) provides a linker length (described below) of 30 Å to 1,000 Å, and it is also preferred to recover a fraction of a molecular weight that corresponds to a desired linker length by gel filtration and to thereby recover a polymer having the below-described linker length.

In addition, as a method of obtaining a maleimidated polymer, there are available a number of conventionally known methods such as a method of obtaining a maleimidated polymer by a single-step dehydration reaction between maleic anhydride and a primary amine ($R1-NH_2$). In this case, the primary amine should be one in which the length from the terminal carbon atom of R1 to the nitrogen atom is 30 Å to 1,000 Å.

As for a method of obtaining the polymer that is aminated, an aminated polymer can be obtained by, for example, a reductive amination reaction between an aldehyde or ketone and a primary amine ($R1-NH_2$). In this case, the total of (1) the length from the carbon atom at one end of the R1 main chain to the carbon atom of the carbonyl group in the molecule of the aldehyde or ketone, (2) the length from the terminal carbon atom of the R1 main chain of the primary amine to the nitrogen atom and (3) the length of the bond between the carbonyl group of (1) and the nitrogen atom of (2) should be 30 Å to 1,000 Å.

As for a method of obtaining the polymer that is biotinylated, a biotinylated polymer can be obtained by biotinylation utilizing Fukuyama coupling (see Shimizu, T.; Seki, M. (2000) "Facile synthesis of (+)-biotin via Fukuyama coupling reaction". Tetrahedron Lett. 41(26): 5099-5101). In this case, the main chain of the molecule to be reacted with biotin should be 30 Å to 1,000 Å.

Further, a method of allowing an alkyl halide (wherein the distance from oxygen of the main chain of R to a halogen atom is 30 Å to 1,000 Å) to react with hydrogen sulfide in the presence of an alkali (R—Br+NaSH→R—SH+NaBr) can also be employed.

(Spacer Length)

When the first hydrophilic polymer is bound to the first binding group substance A such as biotin and the probe biological substance 3 such as an antibody as shown in FIG. 1, the term "spacer length" means the length of a chemical structure part (spacer 1) derived from the first hydrophilic polymer between the first binding group substance A and the probe biological substance 3.

Referring to the specific example of a PEG linker shown in FIG. 2(A), biotin is bound to one end of the PEG linker (the right end of the molecule shown in FIG. 2(A)) and a maleimide group is bound to the other end of the PEG linker (the left end of the molecule shown in FIG. 2(A)). When the probe biological substance 3 such as an antibody is allowed to react with and bound to the maleimide group at the end of this PEG linker, the length of the first hydrophilic polymer-derived spacer (length of the spacer 1) is, as shown in FIG. 2(B), the length of the part from the nitrogen atom of an amide bond and the oxygen atom of the next amide bond, which corresponds to the part indicated by the bidirectional arrow.

Figure 2:
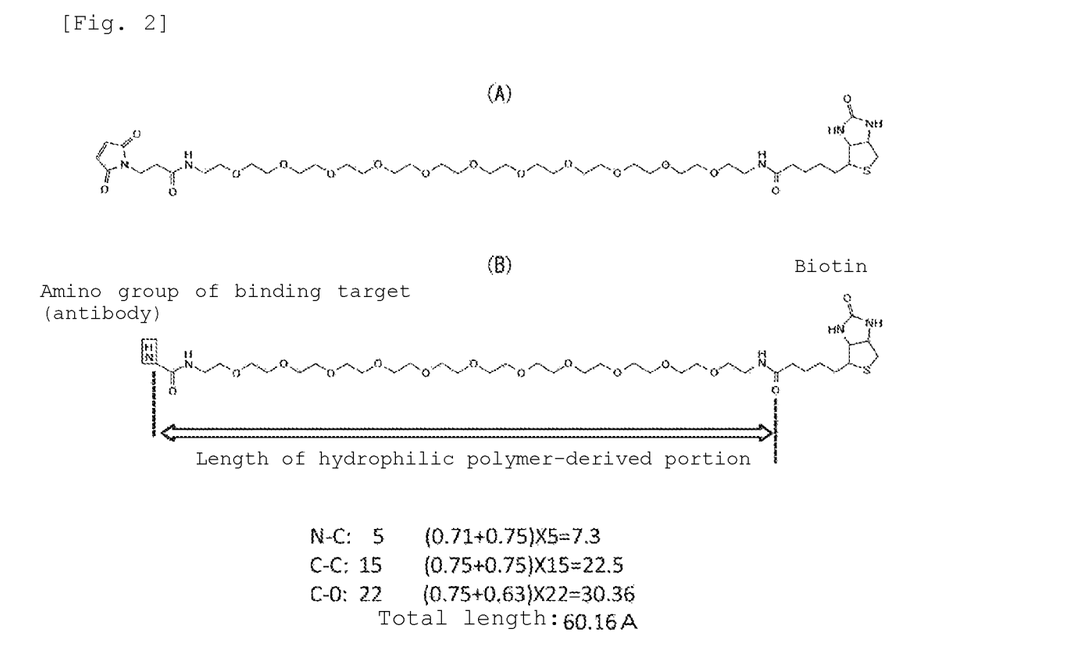
FIG. 2(A) shows a linker to which biotin (first binding group substance) is bound at one end.
FIG. 2(B) is a drawing that shows a state in which the other end of the linker shown in FIG. 2(A) is bound to an antibody (probe biological substance) and illustrates the length of a polymer-derived portion (spacer length).
Figure 3:
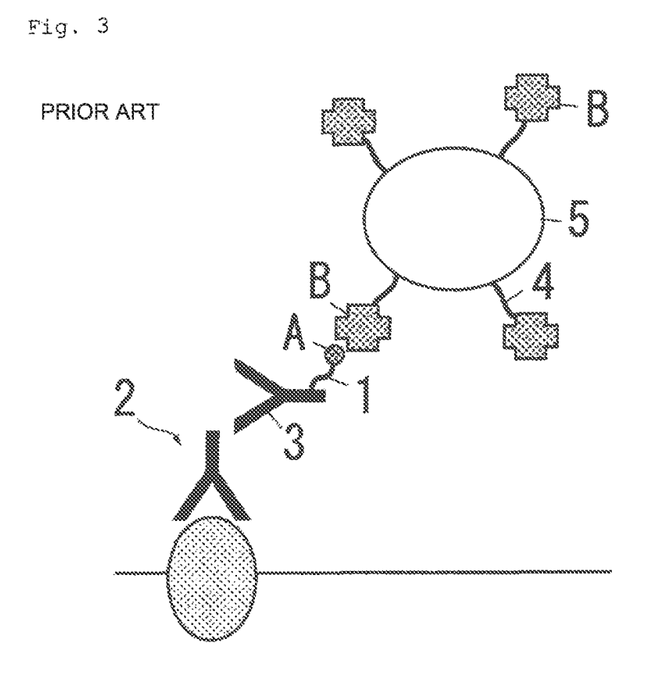
FIG. 3 is a drawing that illustrates a state of immunofluorescent staining performed using a phosphor-integrated nanoparticle labeling agent of prior art.

It is noted here that the lengths of chemical bonds are theoretical values based on a self-consistent approach. According to the theoretical values, the N—C bond length is 1.46 Å; the C—C bond length is 1.50 Å; and the C—O bond length is 1.38 Å. The part of the spacer 1, which is the part from the nitrogen atom of an amide bond and the oxygen atom of the next amide bond as indicated by the bidirectional arrow in FIG. 2(B), contains 5 N—C bonds, 15 C—C bonds and 22 C—O bonds. Accordingly, as shown in FIG. 2, the spacer length is a total theoretical value of 60.16 Å.

The length of the spacer 1 is preferably 33.6 Å to 980.7 Å, more preferably 33.6 Å to 104.7 Å, particularly preferably 55.5 Å to 104.7 Å.

By controlling the length of the spacer 1 to be 30 Å or longer, when immunofluorescent staining is performed, the efficiency of the reaction between the first binding group substance A that is linked to the probe biological substance 3 bound to the biomolecule 2 and the second binding group substance B linked to the phosphor-integrated nanoparticle 5 can be increased and the signal intensity can be improved as a result. In other words, when a biomolecule to be detected is present, the certainty of the presence to be indicated by a bright spot of the phosphor-integrated nanoparticle can be improved. Meanwhile, when the length of the spacer 1 is greater than 1,000 Å (e.g., about 1,500 Å), the spacer 1 is likely to non-specifically adsorb to the interstitial tissue in a tissue section of connective tissue, adipose tissue or the like where hydrophobic amino acids are contained at a high ratio or other sites where the biomolecule 2 is absent. Consequently, even when the probe biological substance 3 is not bound to the biomolecule 2, that is, even in those parts where the biomolecule 2 is absent, bright spots may appear and the noise may thus be increased. The extent of such non-specific adsorption can be examined by, for example, performing immunofluorescent staining on cells not expressing the target biomolecule 2. Therefore, as long as the length of the spacer 1 is in the above-prescribed range, an improvement in the resulting fluorescence signal and inhibition of noise can be preferably balanced, and excellent properties of quantifying the biomolecule 2, such as a disease-associated antigen, can be attained.

The above-described PEG linker and the like can be, for example, purchased as commercial products from Thermo Fisher Scientific K.K. and the like, or obtained by requesting a reagent manufacturer or the like for the production with setting the number of repeating units of the chemical structure contained in the first hydrophilic polymer being set such that the resulting spacer 1 formed by chemical bonding of the first hydrophilic polymer as described above has a length of 30 Å to 1,000 Å.

In addition, the PEG linker and the like may also be obtained by selecting a commercially available polymer as the first hydrophilic polymer such that the resulting spacer 1 formed by chemical bonding of the first hydrophilic polymer as described above has a length of 30 Å to 1,000 Å, subjecting a solution of this first hydrophilic polymer to molecular weight fractionation (e.g., gel filtration) to recover only the first hydrophilic polymer having a prescribed molecular weight and then adding the first binding group substance A and the probe biological substance 3 to the thus recovered first hydrophilic polymer to form the spacer 1. Here, the length of the first hydrophilic polymer-derived spacer 1 can be verified by, for example, subjecting the thus obtained complex (reagent II) of the probe biological substance 3, spacer 1 and first binding group substance A to mass spectrometry by MALDI-TOFMS.

The linker is preferably, for example, as shown in FIG. 2(A), one in which the first binding group substance A (biotin in the example shown in FIG. 2(A)) and a functional group (maleimide group in the example shown in FIG. 2(A)) that reacts with and binds to the probe biological substance (secondary antibody in the example shown in FIG. 2(A)) are bound to each end of the first hydrophilic polymer 1. This is because, for instance, when the first binding group substance A and the functional group are arranged at one end and in the center of the linker, respectively, the length of the spacer 1 corresponds to the length from the one end to the center of the linker and the part from the center to the other end of the linker thus does not function as a spacer. Such a first hydrophilic polymer having a functional group at both ends can be purchased from, for example, a commonly known reagent manufacturer (Thermo Fisher Scientific K.K.).

<<First Binding Group Substance>>

The first binding group substance A is, for example, avidin, biotin, streptavidin, NeutrAvidin, a hapten or an anti-hapten antibody and, as shown in FIG. 1, it is a molecule that specifically binds to the second binding group substance B bound to the below-described phosphor-integrated nanoparticle 5. Examples of the hapten include DIG (digoxigenin), FITC (fluorescein isothiocyanate) and DNP (dinitrophenol).

The bond between the spacer 1 and the first binding group substance A is a bond formed by an appropriate bonding mode such as covalent bonding, ionic bonding, hydrogen bonding, coordinate bonding, physical adsorption or chemical adsorption and, from the standpoint of the bonding strength, the bond is preferably a covalent bond such as an amide bond, an ester bond, an imide bond or a bond utilizing addition of thiol to a maleimide group.

Specific examples of a method for chemically bonding the first hydrophilic polymer and the first binding group substance A include a thiol group-maleimide group coupling reaction method; a cross-linking reaction method using a cross-linking agent (e.g., 1-ethyl-3-(3-dimethylaminopropyl)carbodiimide (EDC)); and an ionic bonding method.

In cases where the first hydrophilic polymer and the first binding group substance A are bound with each other by a cross-linking reaction method, as in the case of the above-described binding of the first hydrophilic polymer-derived 5 linker 1 and the probe biological binding substance 3, it is preferred that the first hydrophilic polymer have a carboxy group at a molecular end. This is because, when a carboxy group is arranged in the central part of the molecular chain of the first hydrophilic polymer, the first binding group substance A may bind to the 10 carboxy group in the central part and a sufficient length may thus not be secured for the first hydrophilic polymer-derived part (the length of the spacer 1 may not be in a range of 30 to 1,000 Å).

<<Second Binding Group Substance>>

The second binding group substance B may be any molecule that specifically binds to the first binding group substance A and it is, for example, biotin, NeutrAvidin, avidin, streptavidin, an anti-hapten antibody or a hapten. Examples of the hapten include DIG (digoxigenin), FITC (fluorescein isothiocyanate) and DNP (dinitrophenol).

(Bond Between Second Binding Group Substance and Phosphor-Integrated Nanoparticle)

The phosphor-integrated nanoparticle 5 and the second binding group substance B may be bound by a direct bond or, as shown in FIG. 1, an indirect bond via other molecule.

Examples of a mode of directly binding the second binding group substance B to the phosphor-integrated nanoparticle 5 include, but not particularly limited to, covalent bonding, ionic bonding, hydrogen bonding, coordinate bonding, physical adsorption and chemical adsorption, which can be performed by a known method. From the standpoint of the binding stability, a bond with high bonding strength, such as a covalent bond, is preferred.

Examples of a mode of indirectly binding the second binding group substance B to the phosphor-integrated nanoparticle 5 include a mode in which a second hydrophilic polymer is bound to the phosphor-integrated nanoparticle 5 and the second binding group substance B and other spacer 4 is thereby allowed to exist between the phosphor-integrated nanoparticle 5 and the second binding group substance B.

As the second hydrophilic polymer, as in the case of the first hydrophilic polymer, one or more hydrophilic polymers selected from the group consisting of polyethylene glycols, ficoll, polypropylene glycols, polyvinyl alcohols, styrene-maleic anhydride alternating copolymers, divinyl ether-maleic anhydride alternating copolymers, polyvinylpyrrolidones, polyvinylmethyl ethers, polyvinylmethyloxazolines, polyethyloxazolines, polyhydroxypropyloxazolines, polyhydroxypropyl methacrylamides, polymethacrylamides, polydimethyl acrylamides, polyhydroxypropyl methacrylates, polyhydroxyethyl acrylates, hydroxymethyl cellulose, hydroxyethyl cellulose, polyaspartoamides, synthetic polyamino acids and equivalents thereof can be used. From the standpoint of inhibiting non-specific adsorption, a polyethylene glycol is preferably used as the second hydrophilic polymer.

As in the case of the above-described bond between the first hydrophilic polymer-derived spacer 1 and the first binding group substance A, the bond between the second hydrophilic polymer-derived spacer 4 and the second binding group substance B is, for example, a bond formed by an appropriate bonding mode such as covalent bonding, ionic bonding, hydrogen bonding, coordinate bonding, physical adsorption or chemical adsorption and, from the standpoint of the bonding strength, the bond is a covalent bond such as an amide bond, an ester bond, an imide bond or preferably a bond utilizing addition of thiol to a maleimide group.

The bond between the second hydrophilic polymer-derived spacer 4 and the phosphor-integrated nanoparticle 5 is not particularly restricted and may be a bond formed by an appropriate bonding mode such as covalent bonding, ionic bonding, hydrogen bonding, coordinate bonding, physical adsorption or chemical adsorption. From the standpoint of the bonding strength, for example, a covalent bond such as an amide bond, an ester bond, an imide bond or a bond utilizing addition of thiol to a maleimide group is preferred. Examples of a method of forming such a bond include a thiol group-maleimide group coupling reaction method; a cross-linking reaction method using a cross-linking agent (e.g., 1-ethyl-3-(3-dimethylaminopropyl)carbodiimide (EDC)); and an ionic bonding method.

<<Phosphor-Integrated Nanoparticle>>

The phosphor-integrated nanoparticle 5 is a particle in which phosphors are integrated. By using such a phosphor-integrated nanoparticle, the amount of fluorescence emitted per molecule, that is, the brightness of a bright spot labeling a prescribed biomolecule can be improved as compared to a single phosphor molecule.

(Phosphor)

The term "phosphor" used herein generally refers to a substance that is excited when irradiated with an X-ray, ultraviolet radiation, visible light, near-infrared radiation or the like from outside and emits light during the transition from the excited state back to the ground state. Accordingly, regardless of the mode of transition from the excited state back to the ground state, the "phosphor" in the present invention may be a substance that emits fluorescence in a narrow sense, which is light emission associated with deactivation from an excited singlet state, or may be a substance that emits phosphorescence, which is light emission associated with deactivation from a triplet state.

Further, the "phosphor" in the present invention is not restricted by the emission lifetime after blocking of the excitation light. Thus, the "phosphor" may be a substance that is known as a light-storing substance, such as zinc sulfide or strontium aluminate. Such phosphors can be generally classified into organic phosphors and inorganic phosphors.

(Organic Phosphor)

Examples of an organic phosphor that can be used as the phosphor include substances known as organic fluorescent dyes, such as fluorescein-based dye molecules, rhodamine-based dye molecules, Alexa Fluor (registered trademark, manufactured by Invitrogen)-based dye molecules, BODIPY (registered trademark, manufactured by Invitrogen)-based dye molecules, Cascade (registered trademark, manufactured by Invitrogen)-based dye molecules, coumarin-based dye molecules, NBD (registered trademark)-based dye molecules, pyrene-based dye molecules, Texas Red (registered trademark)-based dye molecules, cyanine-based dye molecules, perylene-based dye molecules and oxazine-based dye molecules.

Specific examples thereof include 5-carboxy-fluorescein, 6-carboxy-fluorescein, 5,6-dicarboxy-fluorescein, 6-carboxy-2',4,4',5',7,7'-hexachlorofluorescein, 6-carboxy-2',4,7,7'-tetrachlorofluorescein, 6-carboxy-4',5'-dichloro-2',7'-dimethoxyfluorescein, naphthofluorescein, 5-carboxy-rhodamine, 6-carboxy-rhodamine, 5,6-dicarboxy-rhodamine, rhodamine 6G, tetramethylrhodamine, X-rhodamine, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 635, Alexa Fluor 647, Alexa Fluor 660, Alexa Fluor 680, Alexa Fluor 700, Alexa Fluor 750, BODIPY FL, BODIPY TMR, BODIPY 493/503, BODIPY 530/550, BODIPY 558/568, BODIPY 564/570, BODIPY 576/589, BODIPY 581/591, BODIPY 630/650, BODIPY 650/665 (all of which are manufactured by Invitrogen), methoxycoumarin, eosin, NBD, pyrene, Cy5, Cy5.5 and Cy7. These organic phosphors may be used individually, or a plurality thereof may be used in combination.

(Inorganic Phosphor)

Examples of an inorganic phosphor that can be used as the phosphor include quantum dots containing a Group II-VI compound, Group III-V compound or Group IV element as a component (hereinafter, such quantum dots are also referred to as "Group II-VI quantum dot", "Group III-V quantum dot" and "Group IV quantum dot", respectively). These quantum dots may be used individually, or a plurality thereof may be used in combination.

Specific examples thereof include, but not limited to, CdSe, CdS, CdTe, ZnSe, ZnS, ZnTe, InP, InN, InAs, InGaP, GaP, GaAs, Si and Ge.

Quantum dots in which any of the above-described quantum dots is used as a core and a shell is provided thereon can also be used. Hereinafter, as a method of describing quantum dots having a shell, a quantum dot whose core is CdSe and shell is ZnS is indicated as "CdSe/ZnS". For example, CdSe/ZnS, CdS/ZnS, InP/ZnS, InGaP/ZnS, Si/SiO$_2$, Si/ZnS, Ge/GeO$_2$ and Ge/ZnS can be used; however, the quantum dot is not restricted thereto.

If necessary, a quantum dot whose surface has been treated with an organic polymer or the like may be used as well. Examples thereof include CdSe/ZnS having surface carboxy groups (manufactured by Invitrogen) and CdSe/ZnS having surface amino groups (manufactured by Invitrogen).

<<Method of Producing Phosphor-Integrated Nanoparticle>>

The method of producing the phosphor-integrated nanoparticle is not particularly restricted, and the phosphor-integrated nanoparticle can be produced by a known method. Generally, a production method in which phosphors are put together using a resin or silica as a matrix (phosphors are immobilized inside or on the surface of the matrix) can be employed.

<When Organic Phosphor is Used>

Examples of a method of producing phosphor-integrated nanoparticles using an organic phosphor include a method of forming resin particles having a diameter in the order of nanometers, in which resin particles a fluorescent dye that is a phosphor is immobilized inside or on the surface of a matrix made of a resin. The method of preparing such phosphor-integrated nanoparticles is not particularly restricted, and it is possible to employ, for example, a method in which a phosphor is added while (co)polymerizing (co)monomers for the synthesis of a resin (thermoplastic resin or thermosetting resin) constituting the matrix of phosphor-integrated nanoparticles and the phosphor is thereby incorporated inside or on the surface of the resulting (co)polymer.

As the thermoplastic resin, for example, polystyrene, polyacrylonitrile, polyfuran, or a resin equivalent thereof can be suitably used. As the thermosetting resin, for example, polyxylene, polylactic acid, glycidylmethacrylate, polymelamine, polyurea, polybenzoguanamine, polyamide, phenol resin, polysaccharide, or a resin equivalent thereof can be suitably used. A thermosetting resin, particularly a melamine resin is preferred because elution of the dye embedded in the dye resin can also be inhibited by processes such as dehydration, clearing and mounting where an organic solvent such as xylene is used.

For example, polystyrene nanoparticles in which an organic fluorescent dye (phosphor) is embedded can be prepared by the copolymerization method described in U.S. Pat. No. 4,326,008 (1982) where an organic dye having a polymerizable functional group is used, or by the method described in U.S. Pat. No. 5,326,692 (1992) where a fluorescent organic dye is impregnated into polystyrene nano-particles.

Meanwhile, silica nanoparticles in which an organic phosphor is immobilized inside or on the surface of a matrix made of silica can also be produced. As for a production method of such silica nanoparticles, reference can be made to the method of synthesizing FITC-containing silica particles described in Langmuir, Vol. 8, p. 2921 (1992). By using a desired fluorescent dye in place of FITC, a variety of fluorescent dye-containing silica nanoparticles can be synthesized.

<When Inorganic Phosphor is Used>

Examples of a method of producing phosphor-integrated nanoparticles using an inorganic phosphor include a method of forming silica nanoparticle in which a quantum dot that is a phosphor is immobilized inside or on the surface of a matrix made of silica. For this production method, reference can be made to the synthesis of CdTe-containing silica nanoparticles described in New Journal of Chemistry, Vol. 33, p. 561 (2009).

Further, examples of a method of producing phosphor-integrated nanoparticles that is different from the above-descried methods include a method of producing phosphor-integrated nanoparticles by treating silica beads with a silane coupling agent to perform terminal amination and then accumulating semiconductor microparticles as terminal carboxy group-containing phosphors on the surfaces of the silica beads via amide bonds.

Examples of other method of producing phosphor-integrated nanoparticles include a method of forming glassy particles in which semiconductor nanoparticles are dispersed and immobilized by a combination of a reverse micelle method and a sol-gel method using, as a glass precursor, a mixture of an organoalkoxysilane that has an organic functional group showing good adsorption to the semiconductor nanoparticles at an end of the molecule and an alkoxide, and subsequently converting the thus formed glassy particles into phosphor-integrated nanoparticles.

Examples of other method of producing phosphor-integrated nanoparticles also include a method of producing phosphor-integrated nanoparticles by mixing amino group-terminated semiconductor nanoparticles and carboxy group-terminated semiconductor nanoparticles in the presence of 1-ethyl-3-(3-dimethylaminopropyl)carbodiimide hydrochloride (EDC) and subsequently allowing the semiconductor nanoparticles to bind with each other via amide bonds.

Further, an aggregate in which inorganic phosphors are immobilized inside or on the surface of a matrix made of a resin can also be produced. For example, quantum dot-containing polymer nanoparticles can be prepared by the method described in Nature Biotechnology Vol. 19, p. 631 (2001) where quantum dots are impregnated into polystyrene nanoparticles.

<<Immunofluorescent Staining Method>>

A tissue immunostaining method (immunofluorescent staining method) using the phosphor-integrated nanoparticle labeling agent of the present invention will now be described.

(1) Deparaffinization Step

A paraffin-coated tissue section of a test subject (human, dog, cat or the like suspected of having a specific disease) is immersed in xylene contained in a vessel to remove paraffin. The temperature of this process is not particularly restricted and may be room temperature. The immersion time is preferably 3 minutes or longer but not longer than 30 minutes. As required, xylene may be replaced during the immersion.

Then, the tissue section is immersed in ethanol contained in a vessel to remove xylene. The temperature of this process is not particularly restricted and may be room temperature. The immersion time is preferably 3 minutes or longer but not longer than 30 minutes. As required, ethanol may be replaced during the immersion.

The pathological section is further immersed in water contained in a vessel to remove ethanol. The temperature of this process is not particularly restricted and may be room temperature. The immersion time is preferably 3 minutes or longer but not longer than 30 minutes. As required, water may be replaced during the immersion.

(2) Antigen Retrieval Step

It is preferred that the antigen to be stained that is contained in the tissue section be retrieved in accordance with a known method. The antigen retrieval conditions are not particularly defined here; however, as an antigen retrieval liquid, for example, a 0.01 M citrate buffer (pH 6.0), 1 mM ethylenediamine tetraacetic acid (EDTA) solution (pH 8.0), 5% urea or 0.1 M Tris-HCl buffer can be used. As a heating equipment, for example, an autoclave, a microwave oven, a pressure cooker or a water bath can be used. The temperature is not particularly restricted, and the antigen retrieval may be performed at room temperature. The heating process of the antigen retrieval can be performed at a temperature of 50 to 130° C. for a period of 5 to 30 minutes.

Then, the thus antigen-retrieved section is immersed and washed in PBS buffer (hereinafter, referred to as "PBS") contained in a vessel. The temperature of this process is not particularly restricted and may be room temperature. The immersion time is preferably 3 minutes or longer but not longer than 30 minutes. As required, PBS may be replaced during the immersion.

(3) Immunostaining Step

In the immunostaining step, the probe biological substance of the phosphor-integrated nanoparticle labeling agent of the present invention is allowed to bind to the antigen or primary to n-order antibody (biomolecule) contained in the tissue section.

Specifically, a buffer (e.g., PBS) dispersion of the phosphor-integrated nanoparticle labeling agent is prepared and placed on the tissue section to allow the probe biological substance of the phosphor-integrated nanoparticle labeling agent to bind to the biomolecule. Then, the thus stained tissue section is immersed in a buffer (e.g., PBS) contained in a vessel to remove unreacted fluorescent nanoparticle labeling agent, antibody and the like. The immersion time is preferably 3 minutes or longer but not longer than 30 minutes. As required, the buffer (e.g., PBS) may be replaced during the immersion. After the immunostaining step, it is desired to further perform a morphological staining step, such as hematoxylin-eosin staining.

(Other Staining)

On another tissue array slide that is derived from the same test subject as a certain tissue array slide, immunochemical staining (e.g., DAB staining) may be performed for verification of the presence or absence of an antigen that is the same as or different from the one subjected to the immunofluorescent staining. Further, a certain tissue array slide may also be double-stained by immunofluorescent staining and immunochemical staining that target different antigens. In these cases, a chromogenic enzyme-bound antibody or the like is allowed to bind to a specific antigen in a pathological section through an antigen-antibody reaction, and a chromogenic substrate is subsequently added to the reaction system to allow the chromogenic enzyme to develop a color.

In the stage of the antigen-antibody reaction, the binding to the antigen can be performed by a known method. Prior to the binding through the antigen-antibody reaction, it is preferred to add dropwise a known blocking agent, such as BSA-containing PBS, to the tissue section and incubate the tissue section at room temperature for a prescribed time (e.g., 1 hour) in advance.

In the color developing process, a color is chemically developed by adding the substrate of the chromogenic enzyme and a color developer to the reaction system, and examples of the color developer include the followings.

When horseradish peroxidase (HRP) is used as the chromogenic enzyme, the color developer may be, for example, TMB (3,3,5,5-tetramethylbenzidine), 3,3'-diaminobenzidine (DAB) or 4-chloro-1-naphthol. When alkaline phosphatase is used as the chromogenic enzyme, the color developer may be, for example, new fuchsine.

(4) Fixation Step

The fixation step is a step of fixing the phosphor-integrated nanoparticle labeling agent and the like introduced by the (3) staining step on the tissue section. Examples of a fixation solution include cross-linking agents and cell membrane permeable substances, such as formalin, paraformaldehyde, glutaraldehyde, acetone, ethanol and methanol. The fixation can be performed by a conventionally known method. Specifically, the fixation can be performed by immersing the stained tissue section obtained by the (3) staining step in the fixation solution. For example, the fixation can be performed by immersing the stained tissue section obtained by the (3) staining step in a dilute aqueous paraformaldehyde solution for about several minutes to several hours.

(5) Observation Step (5-1) Bright-Field Observation Step

The bright-field observation step is a step of, after the staining (e.g., morphological staining, enzyme immunostaining) performed in the above-described steps (1) to (4) using a color developer (dye) that can be observed as a visible light, irradiating the thus stained tissue section with an illumination light, observing the dye of the color developer deposited on the tissue section and thereby acquiring information on the distribution of the antigen to be stained in cells or tissue (e.g., the number of colored spots).

Eosin used for morphological staining not only is observable in a bright field but also emits intrinsic fluorescence when irradiated with an excitation light of a prescribed wavelength; therefore, eosin can also be observed under a fluorescence microscope. The excitation light may be any light as long as it allows the tissue as well as eosin used as required to emit intrinsic fluorescence of a desired wavelength, and the means for irradiating the excitation light is also not particularly restricted. For example, from a laser light source installed in a fluorescence microscope, an excitation light having an appropriate wavelength and output may be irradiated to the stained tissue section using, as required, a filter which selectively allows light having a prescribed wavelength to pass therethrough.

As cell morphology information, it is suitable to obtain cell morphology information contained in a fluorescence viewing field. Needless to say, if necessary, for example, by using an appropriate filter that is capable of sufficiently reduce either the autofluoresence of the tissue or the fluorescence emitted by a fluorescent labeling material, only the cell morphology information is preferably obtained in a single viewing field.

Meanwhile, in the bright-field observation where, for example, HER2 protein in breast cancer is the biomolecule to be detected and histochemical staining (e.g., DAB staining) is performed thereon as the above-described other staining, a positively stained image of HER2 protein of the cancer cells in a sample tissue, the strength of the positive stain and the ratio of positive cells are observed under an appropriate illumination light using a ×4 objective lens on a light microscope. Then, the objective lens is switched to a ×10 objective lens to verify whether the positive findings are localized in the cell membrane or cytoplasm and, as required, a further observation is made using a ×20 objective lens.

In all of the above-described bright-field observations, a bright-field image may be obtained through the lens barrel of a microscope so as to allow prompt observation, or an image taken by a camera mounted on a microscope may be displayed and observed on a separate display means (e.g., a monitor).

(5-2) Fluorescence Observation Step

The fluorescence observation step is a step of irradiating an excitation light to the phosphor of the phosphor-integrated nanoparticles contained in the tissue section stained by the above-described step and thereby acquiring information on the biomolecule distribution (e.g., the number of bright spots) based on the fluorescence emitted by the phosphor.

As the excitation light, one suitable for the phosphor is irradiated to excite the phosphor, and the biomolecule to be stained is thereby fluorescently stained. The means for irradiating the excitation light is not particularly restricted. For example, from a laser light source installed in a fluorescence microscope, an excitation light having an appropriate wavelength and output may be irradiated to the stained tissue section using, as required, a filter which selectively allows light having a prescribed wavelength to pass therethrough.

The excitation light is not particularly restricted as long as the fluorescence emitted by the phosphor can be distinguished from the intrinsic fluorescence of the tissue section; however, from the standpoint of preventing the intensity of the intrinsic fluorescence emitted by the tissue section from being excessively high, an excitation light having a wavelength of 450 nm to 700 nm is preferred. Further, as a fluorescent substance constituting the phosphor, a substance that emits fluorescence with a peak in a range of 480 nm or longer, preferably in a range of 580 to 690 nm, when irradiated with the excitation light, is used (accordingly, the fluorescence having an emission wavelength in this range is measured).

Further, in this step, information on the biomolecule distribution may be acquired through the lens barrel of a (fluorescence) microscope so as to allow prompt observation, or an image taken by a camera mounted on a (fluorescence) microscope may be displayed and observed on a separate display means (e.g., a monitor). Depending on the fluorescent substance constituting the phosphor used as a label, even when information on the biomolecule distribution cannot be adequately acquired visually through the lens barrel of a microscope, information on the biomolecule distribution can be acquired from an image taken by a camera in some cases.

For acquisition of the information on the biomolecule distribution, for example, the number or density of the biomolecules to be stained per cell is measured based on the number of fluorescent bright spots or the luminescence brightness. For excitation of the phosphor, an excitation light source and an optical filter for fluorescence detection that conform to the maximum absorption wavelength and the fluorescence wavelength can be selected. For the measurement of the number of bright spots or the luminescence brightness, it is preferred to use a commercially available image analysis software (e.g., an automatic total bright spot measuring software "G-Count" (manufactured by G-Angstrom K.K.)); however, the measuring means is not particularly restricted.

The actions and effects of the phosphor-integrated nanoparticle labeling agent of the present invention and an immunofluorescent staining method using the same will now be described.

(1) The phosphor-integrated nanoparticle labeling agent of the present invention comprises a set composed of: a probe biological substance 3, which is linked to a first binding group substance A via a hydrophilic polymer-derived spacer 1 of a prescribed length and specifically binds to a biomolecule 2, such as an antigen or a primary to n-order antibody; and a phosphor-integrated nanoparticle 5, to which a second binding group substance B capable of specifically binding to the first binding group substance A is bound (see FIG. 1).

By controlling the length of the spacer 1 derived from a first hydrophilic polymer to be not shorter than a prescribed value (30 Å), when immunofluorescent staining is performed, the efficiency of the reaction between the first binding group substance A that is linked to the probe biological substance 3 bound to the biomolecule 2 and the second binding group substance linked to the phosphor-integrated nanoparticle 5 is increased and the signal is thus improved and, by controlling the length of the spacer 1 to be not longer than a prescribed value (1,000 Å), a reduction in the reaction efficiency and non-specific adsorption are inhibited, so that noise can be reduced. Consequently, the detection sensitivity and quantitative accuracy of the biomolecule 2 such as a disease-associated antigen are improved and the reliability of the pathological assessment can thus be improved.

(2) As long as the spacer 1 is derived from a hydrophilic polymer (first hydrophilic polymer) such as highly hydrophilic polyethylene glycol (PEG), non-specific adsorption of a complex (reagent II) of the probe biological substance 3, spacer 1 and first binding group substance A to interstitial cells constituted by hydrophobic tissue can be inhibited. This is also advantageous in that the length of the spacer 1 can be easily adjusted by changing the number of oxyethylene units.

(3) As long as the spacer 1 is derived from polyethylene glycol (PEG) and the number of oxyethylene units (n) of this spacer 1 is 6 to 230, the effects of inhibiting the non-specific adsorptions of the above (1) and (2) can be particularly improved.

(4) When the first binding group substance A and B are each biotin or streptavidin, the bond between these molecules is extremely specific; therefore, the effects of the above (1) are improved.

Further, when the first binding group substance A and B are biotin and streptavidin, respectively, the molecular size of the complex (reagent II) of the probe biological substance 3, spacer 1 and first binding group substance A as a whole can be reduced as compared to a case where the first binding group substance A and B are streptavidin and biotin, respectively; therefore, there is an advantage in that, in immunofluorescent staining, the antigen-antibody reaction between the biomolecule 2 and the probe biological substance 3 is unlikely to be adversely affected.

(5) By allowing the phosphor-integrated nanoparticle 5 to have an average particle size of 50 nm to 200 nm, fluorescence observation can be performed under a general-purpose microscope. When the average particle size of the phosphor-integrated nanoparticle 5 is smaller than 50 nm, it is difficult to observe bright spots under a general-purpose microscope in fluorescence observation. Meanwhile, when the average particle size of the phosphor-integrated nanoparticle is larger than 200 nm, the binding efficiency between the phosphor-integrated nanoparticle and the probe biological substance via the binding of the first and second binding group substances is reduced.

(6) As long as the length of the spacer 1 is 50 Å to 100 Å, particularly the effects of the above (1) can be improved.

(7) Since the biomolecule may be an antigen or a primary to n-order antibody and the probe biological substance may be a primary or secondary to (n+1)-order antibody, the phosphor-integrated nanoparticle labeling agent of the present invention can be used in various embodiments of immunofluorescent staining.

EXAMPLES

Example 1

<<Production of Streptavidin-Bound Texas Red Dye-Containing Melamine Resin Nanoparticles>>

After dissolving 2.5 mg of Sulforhodamine 101 (Texas Red dye, manufactured by Sigma-Aldrich) in 22.5 mL of pure water, the resulting solution was stirred for 20 minutes using a hot stirrer with the temperature of the solution being maintained at 70° C. Then, 1.5 g of a melamine resin "Nikalac MX-035" (manufactured by Nippon Carbide Industries Co., Ltd.) was added to the solution, and the resultant was further stirred with heating for 5 minutes under the same conditions.

To the thus heat-stirred solution, 100 μL of formic acid was added, and the resulting solution was stirred for 20 minutes with its temperature being maintained at 60° C. Then, the solution was left to stand and allowed to cool to room temperature. The thus cooled solution was dispensed into a plurality of centrifuge tubes and centrifuged for 20 minutes at 12,000 rpm to allow Texas Red dye-containing melamine resin nanoparticles contained as a mixture in the solution (hereinafter, abbreviated as "particles X") to precipitate, followed by removal of the resulting supernatant. Then, the thus precipitated particles X were washed with ethanol and water.

After the washing, 0.1 mg of the particles X was dispersed in 1.5 mL of ethanol, and 2 μL of aminopropyltrimethoxysilane LS-3150 (manufactured by Shin-Etsu Chemical Co., Ltd.) was added thereto. The resulting mixture was allowed to react with stirring for 8 hours at room temperature to perform a surface amination treatment.

The concentration of the thus surface-aminated particles X was adjusted to 3 nM using PBS containing 2 mM of EDTA (ethylenediamine tetraacetic acid), and this solution was mixed with a linker reagent "SM(PEG)$_{12}$" (manufactured by Thermo Fisher Scientific K.K., cat. No. 22112) to a final concentration of 10 mM. The resulting mixture was allowed to react with stirring at room temperature for 1 hour.

The thus obtained reaction liquid was centrifuged at 10,000 G for 20 minutes and the resulting supernatant was removed. Then, PBS containing 2 mM of EDTA was added to disperse the precipitates, and the resulting dispersion was centrifuged again under the same conditions. The precipitates were washed three times by the same procedure to obtain particles X surface-treated with PEG chains having a maleimide group at a terminal.

Meanwhile, sulfhydryl group-containing streptavidin was prepared as follows. First, 70 μL of N-succinimidyl-S-acetylthioacetate (SATA, manufactured by Pirce) adjusted to a concentration of 64 mg/mL was allowed to react with 40

μL of streptavidin (manufactured by Wako Pure Chemical Industries, Ltd.) adjusted to a concentration of 1 mg/mL for 1 hour at room temperature. In other words, a protected thiol group (—NH—CO—CH$_2$—S—CO—CH$_3$) was introduced to the amino group of streptavidin.

Then, by a known hydroxylamine treatment, a free thiol group (—SH) was generated from the protected thiol group to perform a process of adding a thiol group (—SH) to streptavidin.

The resulting streptavidin solution was desalted through a gel filtration column (Zaba Spin Desalting Columns: manufactured by Funakoshi Co., Ltd.) to obtain streptavidin capable of binding to the particles X surface-treated with PEG chains having a maleimide group at a terminal.

The particles X surface-treated with PEG chains having a maleimide group at a terminal and the above-described SH group-added streptavidin were mixed in PBS containing 2 mM of EDTA and allowed to react for 1 hour. Then, the reaction was terminated by adding 10 mM mercaptoethanol. After concentrating the resulting solution using a centrifugation filter, unreacted streptavidin and the like were removed using a purification gel-filtration column, thereby obtaining particles X (reagent III) having PEG (33.6 Å) with a streptavidin (second binding group substance)-modified terminal.

(Method of Measuring Average Particle Size of Fluorescent Nanoparticles)

A photograph of the phosphor-integrated nanoparticles was taken under a scanning electron microscope (SEM), the cross-sectional area was measured for a sufficient number of particles, and the size of each particle was determined as the diameter of a circular area corresponding to the respective measured value. Specifically, the arithmetic mean of the particle size of 1,000 phosphor-integrated nanoparticles was defined as the average particle size. The phosphor-integrated nanoparticles of Example 1 had an average particle size of 150 nm.

<<Preparation of Biotin-Modified Secondary Antibody>>

In a 50 mM Tris solution, 50 μg of an anti-rabbit IgG antibody was dissolved. A DTT (dithiothreitol) solution was mixed therewith to a final concentration of 3 mM. Then, the resulting solution was allowed to react at 37° C. for 30 minutes, and a DTT-reduced secondary antibody was subsequently purified using a desalting column. Of the whole amount of the thus purified antibody, 200 μL was dissolved in a 50 mM Tris solution to obtain an antibody solution. Meanwhile, a linker reagent having a spacer length of 30 Å, "Biotin-PEG$_6$-NH-Mal" (manufactured by PurePEG, LLC.; product No. 2461006-250), was adjusted with DMSO to a concentration of 0.4 mM. This solution in an amount of 8.5 μL was added to the antibody solution, and the resultant was allowed to react with mixing at 37° C. for 30 minutes.

The thus obtained reaction solution was applied to a desalting column "Zeba Desalting Spin Columns" (manufactured by Thermo Fisher Scientific K.K., Cat.#89882) and purified. The absorption of the thus desalted reaction solution at a wavelength of 300 nm was measured using a spectrophotometer ("F-7000", manufactured by Hitachi, Ltd.) and the amount of proteins contained in the reaction solution was calculated. The reaction solution was adjusted with a 50 mM Tris solution to a concentration of 250 μg/mL, and the resulting solution was used as a solution of a biotinylated secondary antibody (reagent II).

<<Immunofluorescent Staining Method>>

(1) Deparaffinization Step

Using the above-described biotinylated secondary antibody and the like, tissue immunostaining and morphological staining of human breast tissue were performed as described below. As a tissue section to be stained, tissue array slides of HER2 (3+) and HER2(−) ("CB-A712 Series", manufactured by Cosmo Bio Co., Ltd.) were used. These tissue array slides were deparaffinized.

Here, the HER2 score of "3+" follows the HER2 Testing Guide (Third Edition) prepared by The Trastuzumab Pathology Committee and indicates that the subject tissue section is confirmed by a DAB method to show "strong, complete membrane staining in >30% of tumor cells". Meanwhile, the HER2 score of "-" indicates that the subject tissue section is one assigned with a score of "0" based on the HER2 Testing Guide (Third Edition) prepared by The Trastuzumab Pathology Committee, that is, among those tissue sections that fall in the criteria of "no staining is observed, or membrane staining is observed in <10% of tumor cells (positive staining confined to cell membrane is excluded from the assessment)", the subject tissue section is one which is confirmed by a DAB method to show "no positive staining in cell membrane".

Such confirmation by DAB staining was performed using other section (tissue array slide) that was derived from the same tissue as the section (tissue array slide) used in each Example.

(2) Antigen Retrieval Step

After the subject tissue array slide was deparaffinized, the tissue array slide was washed by substitution with water. The thus washed tissue array slide was subjected to a 15-minute autoclave treatment at 121° C. in 10 mM citrate buffer (pH 6.0), thereby performing an antigen retrieval treatment. After the antigen retrieval, the tissue array slide was washed with PBS and then subjected to a 1-hour blocking treatment with 1% BSA-containing PBS.

(3) Immunostaining Step (3-1) Primary Reaction

Using 1% BSA-containing PBS, an anti-HER2 rabbit monoclonal antibody "4B5" (reagent I) manufactured by Ventana Medical Systems, Inc. was adjusted to a concentration of 0.05 nM, and the thus obtained primary antibody solution was allowed to react with the thus block-treated tissue array slide at 4° C. overnight.

(3-2) Secondary Reaction

The tissue array slide subjected to the primary reaction was washed with PBS and subsequently allowed to react with the above-described biotinylated secondary antibody (reagent II), which had been diluted with 1% BSA-containing PBS to a concentration of 6 μg/mL, at room temperature for 30 minutes.

(3-3)

The tissue array slide subjected to the secondary reaction was further allowed to reaction with the above-described phosphor-integrated nanoparticles (reagent III), which had been diluted with 1% BSA-containing PBS to 0.02 nM, under a neutral pH environment (pH=6.9 to 7.4) at room temperature for 3 hours. Thereafter, the resulting tissue array slide was washed with PBS.

(4) Morphological Staining Step

After the immunostaining, hematoxylin-eosin staining (HE staining) was performed. The immunostained section was subjected to hematoxylin staining for 5 minutes with Mayer's hematoxylin solution and then washed with 45° C. running water for 3 minutes. Subsequently, the section was subjected to eosin staining for 5 minutes with 1% eosin solution.

(5) Fixation Step

After the immunostaining and morphological staining steps, an operation of immersing the tissue section in pure ethanol for 5 minutes was repeated four times to perform washing and dehydration. Subsequently, an operation of immersing the tissue section in xylene for 5 minutes was repeated four times to perform clearing. Lastly, the tissue section was mounted with amounting medium ("Entellan New", manufactured by Merck KGaA) to prepare a sample tissue array slide for observation.

(6) Observation and Measurement Step

The tissue section subjected to the fixation step was irradiated with a prescribed excitation light to allow fluorescence to be emitted. The tissue section in this state was observed and photographed under a fluorescence microscope ("BX-53", manufactured by Olympus Corporation) using a microscope digital camera ("DP73", manufactured by Olympus Corporation). The excitation light was set to have a wavelength of 575 to 600 nm through an optical filter. In addition, the wavelength range (nm) of the fluorescence to be observed was set to be 612 to 692 nm through an optical filter. The conditions of the excitation wavelength in the microscope observation and image acquisition were set such that the irradiation energy in the vicinity of the center of the visual field was 900 W/cm$^2$ for excitation at 580 nm. In the image acquisition process, a photograph was taken by arbitrarily setting the exposure time such that the image brightness was not saturated (for example, the exposure time was set at 4,000 μs). The number of bright spots for HER2(3+) and HER(-) tissues was defined as an average value for 1,000 cells, which was determined by an ImageJ Find Maxima method based on an image taken at a magnification of ×400. Further, from the photographed image, the average brightness per bright spot was calculated.

(Discussion)

The results of Example 1 are shown in Table 2.

(Average Number of Bright Spots Per Cell of HER2 (3+) Cell Section)

The evaluation criteria for the average number of bright spots per cell of HER2(3+) cell section were set as follows: an evaluation of "x" was given when the number of bright spots was less than 2 (when the binding affinity to the HER2 antigen to be detected was relatively low, that is, the signal was low); an evaluation of "○" was given when the number of bright spots was 2 to less than 5 (when the binding affinity to the HER2 antigen to be detected was relatively high, that is, the signal was high); and an evaluation of "⊚" was given when the number of bright spots was 5 or greater (when the binding affinity to the HER2 antigen to be detected was extremely high, that is, the signal was extremely high).

In Example 1, when the tissue immunostaining was performed using a spacer 1 whose structural unit was PEG and length (length of the first hydrophilic polymer-derived portion) was 30 Å, the tissue section of HER2(3+) had an average number of bright spots per cell of "2.4" and was thus evaluated as "○".

(Average Number of Bright Spots Per Cell of HER2 (-) Cell Section)

Meanwhile, the evaluation criteria for the average number of bright spots per cell of HER2(-) cell section were set as follows: an evaluation of "○" was given when the number of bright spots was 1 or less (when non-specific adsorption was unlikely to occur, that is, noise was low); and an evaluation of "⊚" was given when the number of bright spots was 0.5 or less (when non-specific adsorption was very unlikely to occur, that is, the signal was extremely low).

In Example 1, the tissue section of normal HER2(-) tissue had an average number of bright spots per cell of "0.3" and was thus evaluated as "⊚".

(Average Brightness Per Bright Spot)

In Example 1, the average brightness per bright spot was "41,200"; therefore, it is seen that sufficient signal was obtained even at a low particle concentration.

(Number of Bright Spots per Image of Interstitial Tissue)

Interstitial tissue is a hydrophobic tissue filling the gaps between cells and does not express the HER2 gene due to the absence of cell nucleus therein. Accordingly, the number of bright spots should naturally be 0 and observation of any bright spot indicates the presence of noise representing non-specific adsorption. Thus, it is required that the number of bright spots attributed to such noise be kept small as much as possible. Here, in the above-described observation and image acquisition, with the number of bright spots observed in an image (1,600 pixels×1,200 pixels) itself taken by the camera "DP73" (manufactured by Olympus Corporation) using a ×40 objective lens being defined as the "number of bright spots per image of interstitial tissue", an evaluation of "○" was given when the number of bright spots was 200 or less (when non-specific adsorption to the hydrophobic part was unlikely to occur, that is, noise was low) and an evaluation of "⊚" was given when the number of bright spots was 100 or less (when non-specific adsorption to the hydrophobic part was very unlikely to occur, that is, the signal was extremely low) (see Table 4). In Example 1, the number of bright spots per image of interstitial tissue was "68" (see Table 4).

Further, the staining properties were comprehensively evaluated based on the above-described evaluations of HER2(3+) and HER2(-). The criteria for the overall evaluation of the staining properties were set as follows: an evaluation of "⊚" was given when the evaluations of HER2 (3+) and HER2 (-) were both "⊚" (overall, very excellent staining properties in terms of the accuracy of positive and negative assessments on overexpression of HER2); an evaluation of "○" was given when neither the evaluation of HER2(3+) nor the evaluation of HER2(-) was "x" (overall, excellent staining properties in terms of the accuracy of positive and negative assessments on overexpression of HER2); and an evaluation of "x" was given when either the evaluation of HER2(3+) or the evaluation of HER2(-) was "x" (overall, poor staining properties in terms of the accuracy of positive and negative assessments on overexpression of HER2). In Example 1, the overall evaluation of the staining properties was "○" (see Table 2).

Example 2

Example 2 was carried out in the same manner as in Example 1, except that a propylene-made linker of 46.2 Å in spacer length was synthesized as described below and used as a linker in place of "Biotin-PEG6-NH-Mal".

(Preparation of Linker)

In hexane, 1,18-octadecanedicarboxylic acid (propylene unit=6) and 5 equivalents of 1,6-diaminohexane (1,6-hexanediamine, propylene unit=2) were allowed to undergo an amidation reaction. The amidation reaction was performed with an addition of 2 equivalents of diisopropylcarbodiimide as a catalyst.

The thus obtained reaction product (propylene unit=8) was purified by silica gel column chromatography and GPC to obtain a hydrocarbon compound (propylene unit=8 equivalents) having an amine at both ends. This aminated synthesis product was allowed to react with 0.5 equivalents of biotin-4-nitrophenyl ester (manufactured by TCI Co., Ltd., product No. B4009) in tetrahydrofuran (THF). The resulting mixture was purified by silica gel column chromatography and GPC to obtain a reaction product whose one end was biotinylated and the other end was amine. The thus obtained reaction product was further allowed to react with 1.2 equivalents of N-succinimidyl-3-maleimidopropionate (manufactured by TCI Co., Ltd., product No. S0427) in THF. The resulting compound was purified by silica gel column chromatography and GPC to obtain a linker (propylene unit=8 equivalents) whose one end was biotinylated and the other end was maleimide.
(Results and Discussion)

In Example 2 where the spacer had a length of 46.2 Å and was made of propylene, the HER2 (3+) tissue section had an average number of bright spots per cell of "2.6" and was thus evaluated as "○". In addition, the HER2(−) tissue section had an average number of bright spots per cell of "0.4" and was thus evaluated as "⊚". The overall evaluation of the staining properties was "○". From these results, it is seen that, when the spacer contained in the phosphor-integrated nanoparticle labeling agent is derived from propylene, as compared to a case where the spacer is derived from PEG, although non-specific adsorption (noise) is slightly increased because of a lower hydrophilicity, the phosphor-integrated nanoparticle labeling agent has substantially the same excellent staining properties.

Example 3

Example 3 was carried out in the same manner as in Example 1, except that "Maleimide-PEG11-Biotin" (manufactured by Thermo Fisher Scientific K.K., product No. 21911) having a spacer length of 55.5 Å was used as a linker in place of "Biotin-PEG6-NH-Mal".
(Results and Discussion)

In Example 3 where a PEG linker having a spacer length of 55.5 Å was used, the HER2 (3+) tissue section had an average number of bright spots per cell of "6.1" and was thus evaluated as "⊚". In addition, the HER2 (−) tissue section had an average number of bright spots per cell of "0.3" and was thus evaluated as "⊚". Moreover, the overall evaluation of the staining properties was "⊚". From these results, it is seen that the phosphor-integrated nanoparticle labeling agent of Example 3 yields a stronger signal than the spacer-containing labeling agent of Example 1 and has very excellent staining properties overall.

Example 4

Example 4 was carried out in the same manner as in Example 1, except that "Biotin PEG Maleimide" (Biotin-PEG-Mal, MW=1,000; manufactured by Nanocs Inc., Cat. No. PG2-BNML-1k) having a spacer length of 94 Å was used as a linker in place of "Biotin-PEG6-NH-Mal".
(Results and Discussion)

In Example 4 where a PEG linker having a spacer length of 104.7 Å was used, the HER2 (3+) tissue section had an average number of bright spots per cell of "8.2" and was thus evaluated as "⊚". In addition, the HER2 (−) tissue section had an average number of bright spots per cell of "0.4" and was thus evaluated as "⊚". Moreover, the overall evaluation of the staining properties was "⊚". From these results, it is seen that the phosphor-integrated nanoparticle labeling agent of Example 4 yields a stronger signal than the spacer-containing labeling agent of Example 1 and has very excellent staining properties overall.

Example 5

Example 5 was carried out in the same manner as in Example 1, except that a propylene-made linker of 55.2 Å in spacer length was synthesized as described below and used as a linker in place of "Biotin-PEG6-NH-Mal".
(Preparation of Linker)

In the preparation of the linker of Example 2, by using 1,12-diaminododecane (1,12-dodecanediamine, propylene unit=4) in place of 1,6-diaminohexane (1,6-hexanediamine, propylene unit=2), a linker in which one end was biotinylated and the other end was maleimide (propylene unit=10 equivalents) was obtained.
(Results and Discussion)

In Example 5 where a propylene linker having a spacer length of 55.2 Å was used, the HER2(3+) tissue section had an average number of bright spots per cell of "6.4" and was thus evaluated as "⊚". In addition, the HER2(−) tissue section had an average number of bright spots per cell of "0.9" and was thus evaluated as "○". The overall evaluation of the staining properties was "○". From these results, it is seen that the phosphor-integrated nanoparticle labeling agent of Example 5 yields a stronger signal than the spacer-containing labeling agent of Example 1 and has very excellent staining properties overall.

Example 6

Example 6 was carried out in the same manner as in Example 1, except that "Biotin PEG Maleimide" (Biotin-PEG-Mal, MW=2,000; manufactured by Nanocs Inc., Cat. No. PG2-BNML-2k) having a spacer length of 202.0 Å was used as a linker in place of "Biotin-PEG6-NH-Mal".
(Results and Discussion)

In Example 6 where a PEG linker having a spacer length of 202.0 Å was used, the HER2 (3+) tissue section had an average number of bright spots per cell of "8.0" and was thus evaluated as "⊚". In addition, the HER2 (−) tissue section had an average number of bright spots per cell of "0.8" and was thus evaluated as "○". The overall evaluation of the staining properties was "○". From these results, it is seen that the phosphor-integrated nanoparticle labeling agent of Example 6 yields a stronger signal than the spacer-containing labeling agent of Example 1 and has very excellent staining properties overall.

Example 7

Example 7 was carried out in the same manner as in Example 1, except that "Biotin PEG Maleimide" (Biotin-PEG-Mal, MW=5,000; manufactured by Nanocs Inc., Cat. No. PG2-BNML-5k) having a spacer length of 494.0 Å was used as a linker in place of "Biotin-PEG6-NH-Mal".
(Results and Discussion)

In Example 7 where a PEG linker having a spacer length of 494.0 Å was used, the HER2 (3+) tissue section had an average number of bright spots per cell of "8.2" and was thus evaluated as "⊚". In addition, the HER2 (−) tissue section had an average number of bright spots per cell of "0.8" and was thus evaluated as "○". The overall evaluation of the staining properties was "○". From these results, it is seen that the phosphor-integrated nanoparticle labeling agent of Example 7 yields a stronger signal than the spacer-containing labeling agent of Example 1 and has very excellent staining properties overall.

Example 8

Example 8 was carried out in the same manner as in Example 1, except that "Biotin PEG Maleimide" (Biotin-PEG-Mal, MW=10,000; manufactured by Nanocs Inc., Cat.

No. PG2-BNML-10k) having a spacer length of 980.7 Å was used as a linker in place of "Biotin-PEG6-NH-Mal".
(Results and Discussion)

In Example 8 where a PEG linker having a spacer length of 980.7 Å was used, the HER2 (3+) tissue section had an average number of bright spots per cell of "6.2" and was thus evaluated as "⊚". In addition, the HER2 (−) tissue section had an average number of bright spots per cell of "0.6" and was thus evaluated as "○". The overall evaluation of the staining properties was "○". From these results, it is seen that the phosphor-integrated nanoparticle labeling agent of Example 8 yields a stronger signal than the spacer-containing labeling agent of Example 1 and has very excellent staining properties overall.

Comparative Example 1

Comparative Example 1 was carried out in the same manner as in Example 1, except that "Maleimide-PEG2-Biotin" (manufactured by Thermo Fisher Scientific K.K., product No. 21901) having a spacer length of 16.1 Å was used as a linker in place of "Biotin-PEG6-NH-Mal".
(Results and Discussion)

In Comparative Example 1 where a PEG linker having a spacer length of 16.1 Å was used, the HER2(3+) tissue section had an average number of bright spots per cell of "1.6" and was thus evaluated as "x". In addition, the HER2(−) tissue section had an average number of bright spots per cell of "0.2" and was thus evaluated as "⊚". The overall evaluation of the staining properties was "x". From these results, it is seen that, as compared to the phosphor-integrated nanoparticle labeling agents of the present invention (Examples), the phosphor-integrated nanoparticle labeling agent of Comparative Example 1 yields a weaker signal and has relatively poor staining properties because the length of its spacer is shorter than the value prescribed in the present invention.

Comparative Example 2

Comparative Example 2 was carried out in the same manner as in Example 1, except that a propylene-made linker of 13.3 Å in spacer length was synthesized as described below and used as a linker in place of "Biotin-PEG6-NH-Mal".
(Preparation of Linker)

In the preparation of the linker of Example 2, by using 1,6-diaminohexane (1,6-hexanediamine) as the hydrocarbon compound having an amine at both ends, a linker in which one end was biotinylated and the other end was maleimide (propylene unit=2 equivalents) was obtained.
(Results and Discussion)

In Comparative Example 2 where a propylene linker having a spacer length of 13.3 Å was used, the HER2(3+) tissue section had an average number of bright spots per cell of "1.4" and was thus evaluated as "x". In addition, the HER2(−) tissue section had an average number of bright spots per cell of "0.8" and was thus evaluated as "○". Further, the overall evaluation of the staining properties was "x". From these results, it is seen that, as compared to the phosphor-integrated nanoparticle labeling agents of the present invention (Examples), the phosphor-integrated nanoparticle labeling agent of Comparative Example 2 yields a weaker signal; and that, since its spacer was derived from propylene, the noise was slightly increased as compared to Comparative Example 1 where the spacer was derived from PEG and thus, overall, the staining properties were relatively poor as in the case of Comparative Example 1.

Comparative Example 3

Comparative Example 3 was carried out in the same manner as in Example 1, except that "Biotin-PEG3-maleimide" (manufactured by ChemPep Inc., Cat. No. 271608) having a spacer length of 22 Å was used as a linker in place of "Biotin-PEG6-NH-Mal".

In Comparative Example 3 where a PEG linker having a spacer length of 20.5 Å was used, the HER2(3+) tissue section had an average number of bright spots per cell of "1.8" and was thus evaluated as "x". In addition, the HER2(−) tissue section had an average number of bright spots per cell of "0.4" and was thus evaluated as "⊚". Further, the overall evaluation of the staining properties was "x". From these results, as in the case of the phosphor-integrated nanoparticle labeling agent of Comparative Example 1, it is seen that the phosphor-integrated nanoparticle labeling agent of Comparative Example 3 also have relatively poor staining properties as compared to the phosphor-integrated nanoparticle labeling agents of the present invention (Examples).

Comparative Example 4

Comparative Example 4 was carried out in the same manner as in Example 1, except that a PEG-made linker of 1,496.5 Å in spacer length was synthesized as described below and used as a linker in place of "Biotin-PEG6-NH-Mal".
(Preparation of Linker)

In the preparation of the linker of Example 2, by mixing equivalent amounts of "poly(ethylene glycol) 2-aminoethyl ether biotin 5300" (manufactured by Sigma-Aldrich, product No. 757772) and "Maleimide PEG NHS" (MW=10,000, manufactured by Nanocs Inc., Cat. No. PG2-MLNS-10k) in tetrahydrofuran (THF) for 30 minutes and subsequently purifying the resultant by GPC (JAIGEL-2.5H, manufactured by Japan Analytical Industry Co., Ltd.), a linker in which one end was biotinylated and the other end was maleimide (polyoxyethylene unit=340 equivalents) was obtained.

(Results and Discussion)

In Comparative Example 4 where a PEG linker having a spacer length of 420 Å was used, the HER2 (3+) tissue section had an average number of bright spots per cell of "6.8" and was thus evaluated as "⊚". In addition, the HER2(−) tissue section had an average number of bright spots per cell of "1.6" and was thus evaluated as "x". Further, the overall evaluation of the staining properties was "x". From these results, it is seen that, as compared to the phosphor-integrated nanoparticle labeling agents of the present invention (Examples), the phosphor-integrated nanoparticle labeling agent of Comparative Example 4 causes greater amount of non-specific adsorption and has relatively poor staining properties because the length of its spacer is longer than the value prescribed in the present invention.

TABLE 2

| | Unit | Number of units | Spacer length (Å) | Average brightness per bright spot | Average number of bright spots per HER2 (3+) cell | | Average number of bright spots per HER2 (−) cell | | Overall evaluation of staining properties | Reagent |
|---|---|---|---|---|---|---|---|---|---|---|
| Example 1 | PEG | 6 | 33.6 | 41,200 | 2.4 | ○ | 0.3 | ◎ | ○ | A4 |
| Example 2 | Propylene | 8 | 46.2 | 40,900 | 2.6 | ○ | 0.4 | ◎ | ○ | A5 |
| Example 3 | PEG | 11 | 55.5 | 42,800 | 6.1 | ◎ | 0.3 | ◎ | ◎ | A6 |
| Example 4 | PEG | 22 | 104.7 | 42,600 | 8.2 | ◎ | 0.4 | ◎ | ◎ | A7 |
| Example 5 | Propylene | 10 | 55.2 | 43,400 | 6.4 | ◎ | 0.9 | ○ | ○ | A8 |
| Example 6 | PEG | 44 | 202.0 | 42,300 | 8.0 | ◎ | 0.8 | ○ | ○ | A9 |
| Example 7 | PEG | 111 | 494.0 | 44,300 | 8.2 | ◎ | 0.8 | ○ | ○ | A10 |
| Example 8 | PEG | 222 | 980.7 | 46,100 | 6.2 | ◎ | 0.6 | ○ | ○ | A11 |
| Comparative Example 1 | PEG | 2 | 16.1 | 32,400 | 1.6 | X | 0.2 | ◎ | X | A1 |
| Comparative Example 2 | Propylene | 2 | 13.3 | 32,300 | 1.4 | X | 0.8 | ○ | X | A2 |
| Comparative Example 3 | PEG | 3 | 20.5 | 36,400 | 1.8 | X | 0.4 | ◎ | X | A3 |
| Comparative Example 4 | PEG | 340 | 1,496.5 | 42,800 | 6.6 | ◎ | 1.6 | X | X | A12 |

The "number of units" represents the number of oxyethylene units when the unit is PEG, or means the number of units composed of three consecutive carbons, not the number of propylene units having a common branched structure, when the unit is propylene.

TABLE 3

| | Reagent | Reagent name (manufacturer, product/catalog No.) |
|---|---|---|
| Example 1 | A4 | Biotin-PEG6-NH-Mal (manufactured by PurePEG, LLC; Item #: 2461006-250) |
| Example 2 | A5 | Synthesized from octadecanedioic acid (1,18-octadecanedicarboxylic acid) and hexamethylenediamine (1,6-hexanediamine) |
| Example 3 | A6 | Maleimide-PEG11-Biotin (manufactured by Thermo Fisher Scientific K.K., product number: 21911) |
| Example 4 | A7 | Biotin PEG Maleimide (Biotin-PEG-Mal, MW = 1,000; manufactured by Nanocs Inc., Cat. No. PG2-BNML-1k) |
| Example 5 | A8 | Synthesized from 1,18-octadecanedicarboxylic acid and 1,12-dodecanediamine |
| Example 6 | A9 | Biotin PEG Maleimide (Biotin-PEG-Mal, MW = 2,000; manufactured by Nanocs, Cat. No. PG2-BNML-2k) |
| Example 7 | A10 | Biotin PEG Maleimide (Biotin-PEG-Mal, MW = 5,000; manufactured by Nanocs Inc., Cat. No. PG2-BNML-5k) |
| Example 8 | A11 | BiotinPEG Maleimide (Biotin-PEG-Mal, MW = 10,000; manufactured by Nanocs Inc., Cat. No. PG2-BNML-10k) |
| Comparative Example 1 | A1 | Maleimide-PEG2-Biotin (manufactured by Thermo Fisher Scientific K.K., product number: 21901) |
| Comparative Example 2 | A2 | Synthesized from 1,6-hexanediamine |
| Comparative Example 3 | A3 | Biotin-PEG3-maleimide (manufactured by ChemPep Inc., Cat. No. 271608) |
| Comparative Example 4 | A12 | Synthesized from poly (ethylene glycol) 2-aminoethyl ether biotin 5300 (manufactured by Sigma-Aldrich, product number: 757772) and Maleimide-PEG-NHS (MW = 10,000; manufactured by Nanocs, Cat. No. PG2-MLNS-10k) |

TABLE 4

| | Unit | Spacer length (Å) | Number of bright spots per image of interstitial tissue | |
|---|---|---|---|---|
| Example 1 | PEG | 33.6 | 68 | ◎ |
| Example 2 | Propylene | 46.2 | 129 | ◎ |
| Example 3 | PEG | 55.5 | 83 | ◎ |
| Example 5 | Propylene | 55.2 | 181 | ○ |

Example 9

As a result of changing the respective phosphor-integrated nanoparticles of Examples 1 to 8 to those having an average particle size of smaller than 50 nm or larger than 200 nm, the use of particles having an average particle size of smaller than 50 nm caused a reduction in the visibility of bright spots under a general-purpose fluorescence microscope, while the use of particles having an average particle size of larger than 230 nm caused a reduction in the efficiency of the binding between each phosphor-integrated nanoparticle and the probe biological substance via the binding of the first and second binding group substances (not shown).

In the above, the phosphor-integrated nanoparticle labeling agent of the present invention and an immunofluorescent staining method using the same were described in detail based on embodiments and examples thereof; however, in the present invention, design modifications can be made as long as they do not deviate from the gist of the present invention described in claims.

DESCRIPTION OF SYMBOLS

1: Spacer
2: Biomolecule
3: Probe biological substance
4: Spacer
5: Phosphor-integrated nanoparticle
A: First binding group substance
B: Second binding group substance

The invention claimed is:

1. A phosphor-integrated nanoparticle labeling agent comprising a set composed of:
   a probe biological substance which is linked to a first binding group substance via a polymer-derived spacer having a length of 30 Å to 1,000 Å, the probe being capable of specifically binding to a biomolecule, wherein the probe biological substance is an antibody, the polymer-derived spacer is a polyethylene glycol (PEG), and the probe biological substance and the first binding group substance are covalently linked to the polymer-derived spacer; and
   a phosphor-integrated nanoparticle which comprises a second binding group substance capable of specifically binding to said first binding group substance, the phosphor-integrated nanoparticle being a melamine resin particle having a fluorescent dye immobilized inside or on a surface of the particle, and the surface of the particle having a surface amination treatment via formic acid and aminopropyltrimethoxysilane.

2. The phosphor-integrated nanoparticle labeling agent according to claim 1, wherein the number of oxyethylene units (n) of said polyethylene glycol (PEG) is 6 to 230.

3. The phosphor-integrated nanoparticle labeling agent according to claim 1, wherein
   said first binding group substance is either one of streptavidin and biotin, and
   said second binding group substance is the other one of streptavidin and biotin.

4. The phosphor-integrated nanoparticle labeling agent according to claim 1, wherein said phosphor-integrated nanoparticle has an average particle size of 50 nm to 230 nm.

5. The phosphor-integrated nanoparticle labeling agent according to claim 1, wherein said polyethylene glycol (PEG) has a spacer length of 50 Å to 120 Å.

6. The phosphor-integrated nanoparticle labeling agent according to claim 1, wherein
   said biomolecule is an antigen or a primary antibody,
   said probe biological substance is a primary antibody or a secondary antibody, and
   said phosphor-integrated nanoparticle labeling agent is used for immunofluorescent staining.

7. The phosphor-integrated nanoparticle labeling agent according to claim 1, wherein
   said first binding group substance is selected from the group consisting of avidin, biotin, streptavidin, NeutrAvidin, a hapten, and an anti-hapten antibody, and
   said second binding group substance is a molecule capable of specifically binding to said first binding group substance and is selected from the group consisting of biotin, NeutrAvidin, avidin, streptavidin, an anti-hapten antibody, and a hapten.

* * * * *